US006126953A

United States Patent [19]

Costa et al.

[11] Patent Number: 6,126,953

[45] Date of Patent: Oct. 3, 2000

[54] FRAGRANCE DELIVERY SYSTEMS FOR PERSONAL CARE ARTICLES

[75] Inventors: Jill Bonham Costa, Cincinnati; John Cort Severns, West Chester; Mark Robert Sivik, Fairfield, all of Ohio

[73] Assignee: The Procter & Gamble Company, Cincinnati, Ohio

[21] Appl. No.: 09/242,651

[22] PCT Filed: Aug. 19, 1997

[86] PCT No.: PCT/US97/14538

§ 371 Date: Mar. 18, 1999

§ 102(e) Date: Mar. 18, 1999

[87] PCT Pub. No.: WO98/07407

PCT Pub. Date: Feb. 26, 1998

Related U.S. Application Data

[60] Provisional application No. 60/024,117, Aug. 19, 1996.

[51] Int. Cl.[7] .............................. A61K 7/00; A61K 7/32; A61K 7/06; A61K 7/46

[52] U.S. Cl. .......................... 424/401; 424/70.1; 424/65; 424/400; 512/18; 512/21; 512/27

[58] Field of Search .................................. 424/401, 400, 424/65; 512/18, 21, 27

[56] References Cited

U.S. PATENT DOCUMENTS

| | | | |
|---|---|---|---|
| 3,779,932 | 12/1973 | Jaggers et al. | 252/108 |
| 3,830,930 | 8/1974 | Moeller et al. | 424/308 |
| 3,849,326 | 11/1974 | Jaggers et al. | 252/89 |
| 3,870,759 | 3/1975 | Inamoto et al. | 260/586 |
| 4,524,018 | 6/1985 | Yemoto et al. | 252/522 |
| 4,994,266 | 2/1991 | Wells | 424/76.7 |
| 5,081,111 | 1/1992 | Akimoto et al. | 525/285 |
| 5,232,612 | 8/1993 | Trinh et al. | 252/8.6 |
| 5,266,592 | 11/1993 | Grub et al. | 514/452 |
| 5,378,468 | 1/1995 | Suffis et al. | 424/401 |
| 5,506,201 | 4/1996 | McDermott et al. | 512/252 |
| 5,626,852 | 5/1997 | Suffis et al. | 424/401 |
| 5,739,100 | 4/1998 | Horino et al. | 512/25 |

FOREIGN PATENT DOCUMENTS

| | | |
|---|---|---|
| 0 786 247 A1 | 7/1997 | European Pat. Off. . |
| 1923223 | 5/1969 | Germany . |
| 2509967 | 3/1975 | Germany . |
| 5-230496 | 9/1993 | Japan . |
| 7-179328 | 7/1995 | Japan . |
| WO 94/06441 | 3/1994 | WIPO . |
| WO 95/04809 | 2/1995 | WIPO . |

OTHER PUBLICATIONS

P.M. Muller, D. Lamparsky *Perfumes Art, Science & Technology* Blackie Academic & Professional (New York, 1994) "Perfumery Applications: Functional Products", J.K. Funesti.

Chem. Abstracts #69416, vol. 117, No. 7, Aug. 17, 1992.

Chem. Abstracts #278389, vol. 119, No. 26, Dec. 27, 1993.

*Primary Examiner*—Shelley A. Dodson
*Attorney, Agent, or Firm*—Richard S. Echler, Sr.; Kim W. Zerby; Jacobus C. Rasser

[57] ABSTRACT

The present invention relates to personal care and personal hygiene articles containing a fragrance delivery system which comprises one or more pro-accords, preferably β-ketoester pro-accords, which are capable of releasing mixtures of fragrance raw materials. The pro-accords which comprise the fragrance delivery systems are useful in delivering sustained fragrances to personal care items inter alia deodorants, anti-perspirants, suntan lotions, hair sprays, mousses, shaving creams, body lotions and creams, depilitories, facial masks, athletic rubs and creams.

20 Claims, No Drawings

FRAGRANCE DELIVERY SYSTEMS FOR PERSONAL CARE ARTICLES

This application claims priority under Title 35, United States Code 119(e) from Provisional Application Ser. No. 60/024,117, filed Aug. 19, 1996, which is a 371 of PCT/US97/14538 filed Aug. 19, 1997.

FIELD OF THE INVENTION

The present invention relates to fragrance delivery systems suitable for use in personal care and personal hygiene articles, inter alia deodorants, anti-perspirants, suntan lotions, hair sprays, mousses, shaving creams, body lotions and creams, depilatories, facial masks, athletic rubs and creams. The fragrance delivery systems comprise one or more pro-accord molecules, each molecule capable of releasing one or more fragrance raw materials. In addition, each pro-accord is capable of releasing a different accord (mixture of fragrance raw materials) if used in a different type of composition (i.e. hair spray vs. roll-on deodorant).

BACKGROUND OF THE INVENTION

Humans have applied scents and fragrances to their skin since antiquity and have used fragrances and scents to enhance the aesthetic quality of their environment inter alia clothing and living space. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modern chemistry, individual components responsible for the odor properties of these resins, gums and oils were isolated and subsequently characterized. Aside from aesthetic-purpose items inter alia fine perfumes, colognes, eau de toilettes, after-shave lotions, a wide variety of personal care or personal hygiene items deliver fragrances and scents to the human body.

It is well known that mixtures of perfume or fragrance raw materials when deposited on hair or skin lose intensity and may change character with time, mainly due to factors such as differential evaporation and surface penetration. Many attempts have been made to minimize these drawbacks, but so far without notable success. Particularly, efforts have been made to prolong the diffusion, as well as to improve other characteristics of fragrance materials, by e.g. increasing the fragrance raw material concentration or by using additives such as silicones, glycerol, polyethylene glycols and so on. Such additions, however, have never been adequate to increase the longevity of the fragrance odor.

Accordingly, there remains a need in the art for a fragrance delivery system which can be formulated into any type of product used to deliver an aesthetically pleasing fragrance to the skin or hair via personal care or personal hygiene article which results in delivery of fragrance raw material mixtures having a lasting fragrance impression, therefore, the fragrance must be slowly released.

BACKGROUND ART

The following relate to the subject matter of fragrance ingredients. U.S. Pat. No. 5,626,852 Suffis et al., issued May 6, 1997; U.S. Pat. No. 5,232,612 Trinh et al., issued Aug. 3, 1996; U.S. Pat. No. 5,506,201 McDermott et al., issued Apr. 9, 1996; U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; WO 95/04,809 published Feb. 16, 1995; and WO 95/16660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention meets the aforementioned needs in that it has been surprisingly discovered that a mixture of perfume or fragrance raw materials (accords) can be released from one precursor pro-accord molecule and that these pro-accords can serve as a fragrance delivery system wherein a varying mixture of the fragrances are released depending upon the structure and design of the pro-accord molecule. These pro-accords provide sustained perfume and fragrance retention when applied to human skin either directly or by way of a personal care or personal hygiene article, said personal care and personal hygiene articles include inter alia deodorants, anti-perspirants, suntan lotions, hair sprays, mousses, shaving creams, body lotions and creams, depilatories, facial masks, athletic rubs and creams, ointments, balms, salves, antiseptic creams, or shampoos. The pro-accords described herein comprise fragrances in a stable, releasable "pro-fragrance" form. In addition, the formulator can design compounds according to the present invention which can deliver different fragrance raw material depending upon the conditions of use. The pro-accords can be formulated into any product deliverable, directly or indirectly, to human skin or hair upon which an aesthetically pleasing scent is desired. Once in contact with human skin or hair, the pro-accord is converted to a fragrance raw material mixture at a rate which provides extended fragrance benefits. The fragrance delivery systems of the present invention can be a mixture of any number of pro-accords and can cover any fragrance "characteristic" or desired fragrance volatility.

The first aspect of the present invention relates to compositions which are applied to human skin or hair, said compositions having increased fragrance retention and fragrance longevity. The suitable compositions of the present invention are inter alia deodorants, anti-perspirants, suntan lotions, hair sprays, mousses, shaving creams, body lotions and creams, depilatories, facial masks, athletic rubs and creams, ointments, balms, salves, antiseptic creams, or shampoos, comprising:

a) at least about 0.01%, preferably from about 0.01% to about 15%, more preferably from about 1% to about 5%, most preferably from about 0.1% to about 1% by weight, of a β-ketoester having the formula:

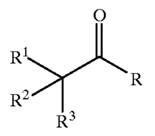

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

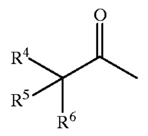

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^4$, $R^5$, and $R^6$ can be taken together to form $C_6$–$C_{30}$ substituted or unsubstituted aryl; and mixtures thereof;

b) at least about 0.01% by weight, of one or more adjunct ingredients selected from the group consisting of surfactants, emollients, bactericides, gelling agents, desiccants, propellants, dyes, colorants, ointment bases, lanolin, antiperspirants, mineral oil, talc, abrasives, optical brighteners, phase stabilizing agents, absorbents, pharmaceutical actives, and mixtures thereof; and c) the balance carriers.

The present invention also relates to methods for providing a fragrance raw material mixture to human skin or hair comprising the step of contacting human skin or hair with the fragrance delivery system of the present invention.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention comprises a fragrance delivery system which lays down one or more fragrance "pro-accord" compounds onto human skin or hair during usage. Because the pro-accords which comprise the fragrance delivery system of the present invention generally have a higher molecular weight than uncombined fragrance raw materials and other "pro-fragrance-type" compounds (i.e. pro-fragrances which only deliver a single equivalent of a fragrance raw material), they are a means for effectively delivering two or more fragrance raw materials which results in enhanced longevity of the fragrance raw materials on a substrate.

Mixtures of fragrance materials are known by those skilled in the art of fragrances and perfumes as "accords". The term "accord" as used herein is defined as "a mixture of two or more 'fragrance raw materials' which are artfully combined to impart a pleasurable scent, odor, essence, or fragrance characteristic". For the purposes of the present invention "fragrance raw materials" are herein defined as compounds imparting an odor, fragrance, essence, or scent either alone or in combination with other "fragrance raw materials" which is considered aesthetically pleasing, preferably said compounds have a molecular weight of at least 100 g/mol.

Typically "fragrance raw materials" comprise inter alia alcohols, ketones, aldehydes, esters, ethers, nitrites, and cyclic and acyclic alkenes, especially terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) both incorporated herein by reference.

For example, but not by way of limitation, the fragrance accords released by the pro-accords of the present invention have a "heart", "character", or "note" which is described as inter alia rose, jasmin, lilac, lily of the valley, violet, orange, peach, watermelon, and lemon, or the pro-accord can deliver fragrance raw materials which provide a "fresh" or "clean" note, for example, linalool or dihydromyrcenol. The accord may be further "modified" or "twisted" by the inclusion of pro-accords which deliver modifier top or middle notes which, as an additional benefit afforded by the present invention, can be incorporated into the pro-accord. For example, a "rose essence" may be combined with a "green" modifier to "shift the fragrance accord character".

For the purposes of the present invention, only fragrance raw materials having a molecular weight of at least 100 g/mol are considered "fragrance raw materials" according to the present invention. Therefore, low molecular weight materials inter alia methanol, ethanol, methyl acetate, ethyl acetate, and methyl formate which are common components of fragrance accords are excluded from the class of compounds defined herein as "fragrance raw materials". However, the formulator may wish to deliver these lower molecular weight materials (less than a molecular weight of 100 g/mol) as carriers, astringents, diluents, balancers, fixatives, or as other suitable adjunct materials.

For the purposes of the present invention the term "pro-fragrance" is defined as "a β-ketoester which releases a fragrance raw material alcohol" whereas a "pro-accord" is defined as "β-ketoester which release two or more fragrance raw materials". For the purposes of the present invention, however, since a material that is a "pro-fragrance" in one embodiment can serve as a "pro-accord" in a different embodiment, the term "pro-fragrance" is used interchangeably with the term "pro-accord" and either term may be used to stand equally well for either β-ketoester pro-fragrance molecules, β-ketoester pro-accord molecules, or both collectively.

For the purposes of the present invention "top note" fragrance raw materials are defined as "fragrances having a high vapor pressure, and when applied to a paper sachet, vaporization takes place within 2 hours, and no scent remains; essentially, the initial impression of the perfume formulation is provided by top notes".

For the purposes of the present invention "middle note" fragrance raw materials are defined as "fragrances having a medium vapor pressure, and when applied to a paper sachet, the scent remains from about 2 to about 6 hours; essentially, middle notes provide the skeleton of the perfume formulation".

For the purposes of the present invention "base note" fragrance raw materials are defined as "fragrances having a low vapor pressure and high retentivity, and when applied to a paper sachet, the scent remains for more than about 6 hours; essentially, base notes provide the characteristic of the perfume formulation.

The terms "top note", "middle note", and "base note" are well recognized by those skilled in the art of fragrance-containing compositions. However, reference to a specific fragrance raw material as a "top note" within the present invention does mean that others skilled in the art of fragrance-containing compositions may not categorized the same ingredient as a "middle note". The same applies to fragrance raw materials referred to as "middle notes" and "base notes".

β-Ketoester Fragrance Delivery System

The fragrance delivery systems of the present invention comprise one or more pro-accords having the formula:

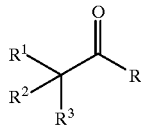

wherein R is alkoxy derived from a fragrance raw material alcohol. Non-limiting examples of preferred fragrance raw material alcohols include 2,4-dimethyl-3-cyclohexene-1-methanol (Floralol), 2,4-dimethyl cyclohexane methanol (Dihydro floralol), 5,6-dimethyl-1-methylethenylbicyclo [2.2.1]hept-5-ene-2-methanol (Arbozol), α,α,-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1.]hept-2-ene-2-ethanol (nopol), 2-(4-methylphenoxy)-ethanol, 3,3-dimethyl-$\Delta^2$-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, 1-phenylpropanol, 3-phenylpropanol, 2-phenylpropanol (Hydrotropic Alcohol), 2-(cyclododecyl) propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamnyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0$^{(2,6)}$]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl4-hexen-1-ol (Lavandulol), 2-ethyl-2-prenyl-3-hexenol, 1-hydroxymethyl-4-isopropenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl) cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1] hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo [3.1.1]heptane, 1,7,7-trimethylbicyclo[2.2.1]heptan-2-ol, 2,6-dimethylheptan-2-ol (dimetol), 2,6,6-trimethylbicyclo [1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6octen-1-ol (citronellol), 3,7-dimethyl-2,6-octadien-1-ol (geraniol), 3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4- vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetrahydrofuran, β-caryophyllene alcohol, vanillin and mixtures thereof.

More preferably, the fragrance raw material alcohol is selected from the group consisting of cis-3-hexen-1-ol, hawthanol [admixture of 2-(o-methylphenyl)ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(1-methylethyl)cyclohexane methanol, 3-(hydroxy-methyl)-2-nonanone, octan-1-ol, 3-phenylpropanol, Rhodinol 70 [3,7-dimethyl-7-octenol, 3,7-dimethyl-6-octenol admixture], 9-decen-1-ol, α-3,3-trimethyl-2-norborane methanol, 3-cyclohexylpropan-1-ol, 4-methyl-1-phenyl-2-pentanol, 3,6-dimethyl-3-vinyl-5-hepten-2-ol, phenyl ethyl methanol; propyl benzyl methanol, 1-methyl-4-isopropenylcyclohexan-3-ol, 4-isopropyl-1-methylcyclohexan-3-ol (menthol), 4-tert-butylcyclohexanol, 2-tert-butyl-4-methylcyclohexanol, 4-isopropylcyclo-hexanol, trans-decahydro-β-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy-4-(1-propenyl)phenol, vanillin, ethyl vanillin, and mixtures thereof.

$R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

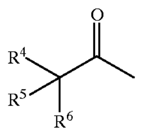

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof.

Preferably at least two $R^1$, $R^2$, or $R^3$ units are hydrogen. In one embodiment of the present invention preferably $R^4$, $R^5$, and $R^6$ units are each hydrogen. In addition, preferably when two $R^4$, $R^5$, and $R^6$ units are hydrogen, the remaining unit is $C_1$–$C_{20}$ substituted or unsubstituted linear alkyl, $C_3$–$C_{20}$ substituted or unsubstituted branched alkyl, $C_3$–$C_{20}$ substituted or unsubstituted cyclic alkyl; more preferably methyl. Also preferably $R^4$, $R^5$, and $R^6$ are taken together to form a $C_6$–$C_{30}$ substituted or unsubstituted aryl unit, preferably substituted or unsubstituted phenyl and naphthyl.

For the purposes of the present invention the term "substituted" as it applies to linear alkyl, branched alkyl, cyclic alkyl, linear alkenyl, branched alkenyl, cyclic alkenyl, branched alkoxy, cyclic alkoxy, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_3$–$C_{12}$ branched alkoxy, preferably isopropoxy; $C_3$–$C_{12}$ cyclic alkoxy; nitrilo; halogen, preferably chloro and bromo, more preferably chloro; nitro; morpholino; cyano; carboxyl, non-limiting examples of which are $—CHO$; $—CO_2^-M^+$, $—CO_2R^9$; $—CONH_2$; $—CONHR^9$; $—CONR^9_2$; wherein $R^9$ is $C_1$–$C_{12}$ linear or branched alkyl); $—SO_3^-M^+$; $—OSO_3^-M^+$; $—N(R^{10})_2$; and $—N^+(R^{10})_3X^-$ wherein each $R^{10}$ is independently hydrogen or $C_1$–$C_4$ alkyl; and mixtures thereof; wherein M is hydrogen or a water soluble cation; and X is chlorine, bromine, iodine, or other water soluble anion.

For the purposes of the present invention substituted or unsubstituted alkyleneoxy units are defined as moieties having the formula:

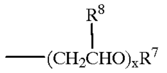

wherein $R^7$ is hydrogen; $R^8$ is hydrogen, methyl, ethyl, and mixtures thereof; the index x is from 1 to about 10.

For the purposes of the present invention substituted or unsubstituted alkyleneoxyalkyl are defined as moieties having the formula:

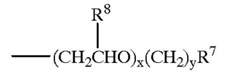

wherein $R^7$ is hydrogen, $C_1$–$C_{18}$ alkyl, $C_1$–$C_4$ alkoxy, and mixtures thereof; $R^8$ is hydrogen, methyl, ethyl, and mixtures thereof; the index x is from 1 to about 10 and the index y is from 2 to about 18.

For the purposes of the present invention substituted or unsubstituted aryl units are defined as phenyl moieties having the formula:

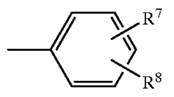

or α and β-naphthyl moieties having the formula:

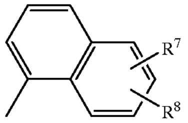

or

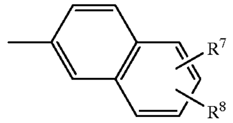

wherein $R^7$ and $R^8$ can be substituted on either ring, alone or in combination, and $R^7$ and $R^8$ are each independently hydrogen, hydroxy, $C_1$–$C_6$ alkyl, $C_2$–$C_6$ alkenyl, $C_1$–$C_4$ alkoxy, $C_3$–$C_6$ branched alkoxy, nitrilo, halogen, nitro, morpholino, cyano, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), —$SO_3^-M^+$, —$OSO^{3-}M^+$, —$N(R^{10})_2$, and —$N^+(R^{10})_3X^-$ wherein each $R^{10}$ is independently hydrogen, $C_1$–$C_4$ alkyl, or mixtures thereof; and mixtures thereof, $R^7$ and $R^8$ are preferably hydrogen, $C_1$–$C_6$ alkyl, —$CO_2^-M^+$, —$SO_3^-M^+$, —$OSO_3^-M^+$, and mixtures thereof; more preferably $R^7$ or $R^8$ is hydrogen and the other moiety is $C_1$–$C_6$; wherein M is hydrogen or a water soluble cation and X is chlorine, bromine, iodine, or other water soluble anion. Examples of other water soluble anions include organic species such as fumarate, succinate, tartrate, oxalate and the like, inorganic species include sulfate, hydrogen sulfate, phosphate and the like.

For the purposes of the present invention substituted or unsubstituted alkylenearyl units are defined as moieties having the formula:

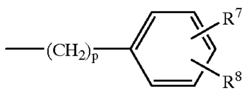

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, p is from 1 to about 14; M is hydrogen or a water soluble cation.

For the purposes of the present invention substituted or unsubstituted alkyleneoxyaryl units are defined as moieties having the formula:

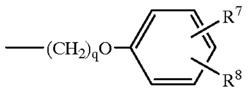

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, q is from 1 to about 14; M is hydrogen or a water soluble cation.

Surprisingly, the pro-accords which comprise the fragrance delivery systems of the present invention are capable of releasing at least one fragrance raw material, preferably the pro-accords release two or more fragrance raw materials. For example, the pro-accord 3,7-dimethyl-1,6-octadien-3-yl 3-(β-naphthyl)-3-oxo-propionate having the formula:

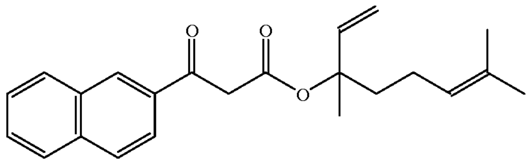

releases, depending upon usage conditions, at least two fragrance raw materials inter alia linalool, β-naphthyl methyl ketone, myrcene, α-terpinolene, and Δ-3-carene.

The pro-accords which comprise the fragrance delivery systems of the present invention are capable of releasing their fragrance compounds by more than a single chemical mechanism, a point which is key to the variety of fragrance raw materials which are released from a single pro-accord compound. Therefore, depending upon the desires of the formulator, the pro-accords of the present invention are capable of releasing a different mixture of fragrance raw materials depending upon the releasing milieu. For example, the pro-accord 3,7-dimethyl-1,6-octadien-3-yl 3-(β-naphthyl)-3-oxo-propionate produces a different accord when undergoing fragrance raw material release upon skin than when undergoing fragrance raw material release on hair. Typically the pro-accords of the present invention release a mixture of alcohols, esters, ketones, hydrocarbyl materials, especially terpenes, having aesthetically pleasing qualities, and mixtures thereof. For the purposes of the present invention the term "hydrocarbyl material" is defined as a compound which essentially comprises only carbon and hydrogen inter alia alkanes, alkenes, and alkynes whether linear, cyclic, branched, or combinations thereof". An example, of a hydrocarbyl material which is capable of being released by a pro-accord of the present invention is myrcene. For the purposes of the present invention the term "terpene" is used to designate hydrocarbons inter alia myrcene, limonene, and α-terpinene. However, those skilled in the art of perfumes as well as organic chemistry recognize that geraniol and nerol which are listed under "fragrance raw material alcohols" herein above are also terpenes. Throughout the present specification the term "terpene" is used interchangeably with "hydrocarbyl" and when "terpene" is used broadly, it refers to all alcohols, ketones, alkenes, etc. that are generally regarded as terpenes, and when the term "terpene" is used narrowly it refers primarily to alkanes, alkenes, etc. having typically 10 carbon atoms (terpenes) or 15 carbon atoms (sesquiterpenes).

Examples of alcohols releasable by the pro-accords are described herein above and are typically the fragrance raw material alcohols which are used to form the parent compounds. However, during the process of fragrance raw material release, these fragrance raw material alcohols are capable of undergoing further modification, including isomerization and/or rearrangement. Therefore, in addition to the original alcohol used to form the parent pro-accord ester, additional alcohols may be formed by transformations which occur during the release process. Depending upon the choices the formulator makes when designing the pro-accord molecules in formulating a fragrance delivery system according to the present invention, these transformations can take place to a greater or lesser degree.

Non-limiting examples of terpenes releasable by the pro-accords of the present invention include the hydrocarbyl materials myrcene, ocimene, β-farnesene, cis-achillene, trans-achillene, carvomenthene, limonene, α-terpinene, γ-terpinene, terpinolene, α-phellandrene, β-phellandrene, 2-carene, 3-carene, α-pinene, β-pinene, camphene, and other terpenes, for example, (−)-(2S,4R)-2-(2-methyl-1-propenyl)-4-methyltetrahydropyran (cis rose oxide), (−)-(2S,4S)-2-(2-methyl-1-propenyl)-4-methyltetrahydropyran (trans rose oxide), 2-methyl-2-vinyl-5-(α-hydroxy-isopropyl)tetrahydrofuran (linalool oxide), and mixtures thereof.

Non-limiting examples of ketones which are releasable by the pro-accords of the fragrance delivery systems of the present invention are α-damascone, β-damascone, δ-damascone, β-damascenone, muscone, 3,3-dimethylbutanone, methyl phenyl ketone (acetophenone), 4-phenylbutan-2-one (benzyl acetone), 2-acetyl-3,3-dimethyl norbomane (camek dh), 6,7-dihydro-1,1,2,3,3-pentamethyl-4(5H) indanone (cashmeran), 4-(1,3)-benzodioxol-5-yl 3-buten-2-one (cassione), 4-(3,4-methylenedioxyphenyl)-2-butanone (dulcinyl), 3-octanone, 6-acetyl-1,2,3,4-tetrahydronaphthalene ketone (florantone t), ethyl-2-n-hexyl acetoacetate (gelsone), 2,6-dimethylundeca-2,6-dien-10-one, 6,10-dimethyl-5,9-undecadien-2-one, 3,3-dimethylcyclohexyl methyl ketone (herbac), 4-(2,6,6-trimethyl-1-cyclohexen-1-yl)-3-buten-2-one (α-ionone), 4-(2,6,6-trimethyl-2-cyclohexen-1-yl)-3-buten-2-one (α-ionone), 3-methyl-4-(2,6,6-trimethyl-1-cyclohexen-1-yl)-3-buten-2-one (δ-methyl ionone), 4-(2,6,6-trimethyl-2-cyclohexen-1-yl)-3-methyl-3-buten-2-one (γ-methyl ionone), 3-methyl-4-(2,6,-trimethyl-2-cyclohexen-1-yl)-3-buten-2-one (irisantheme), 4-(2,3,5-trimethyl-4-cyclohexen-1-yl)-3-buten-2-one (iritone), 4-methyl-(2,5,6,6-tetramethyl-2-cyclohexen-1-yl)-3-buten-2-one (α-ionone), 1,2,3,4,5,6,7,8-octahydro-2,3,8,8-tetramethyl-2-acetonaphthone (iso cyclomone e), 7-acetyl-1,2,3,4,5,6,7,8-octahydro-1,1,6,7-tetramethyl naphthalene (Iso E Super®), acetyl diisoamylene (Koavone®), methyl amyl ketone, 2-acetonaphthone cedr-8-enyl methyl ketone (methyl cedrylone), 2,3,6-trimethyl-cyclohexen-4-yl-1-methyl ketone (methyl cyclo citrone), hexahydroacetophenone (methyl cyclohexyl ketone), 6-methyl-3,5-heptadien-2-one, 6-methyl-5-hepten-2-one, 2-octanoe, 3-(hydroxymethyl)-2-nonanone, 4-acetyl-1,1-dimethyl-6-tert-butyl indane (musk indanone), 2,6-dinitro-3,5-dimethyl-4-acetyl-tert-butyl benzene (musk ketone), 1-para-menthen-6-yl propanone (nerone), para-methoxy acetophenone (acetanisole), 6-acetyl-1,1,2,3,3,5-hexamethyl indan (Phantolid®), 7-acetyl-1,1,3,4,4,6-hexamethyl tetralin (Tonalid®, Musk Plus®), 5-acetyl-3-isopropyl-1,1,2,6-tetramethyl indane (Traseolide 70®), methyl-2,6,10-trimethyl-2,5,9-cyclododecatriene-1-yl ketone (Trimofix O®), methyl cedrylone (Vertofix Coeur®), 4-(4-hydroxy-3-methoxyphenyl)-2-butanone, cis-jasmone, dihydrojasmone, α-ionone, β-ionone, dihydro-β-ionone, 4-(4-hydroxyphenyl)butan-2-one, l-carvone, 5-cyclohexadecen-1-one, decatone, 2[2-(4-methyl-3-cyclohexenyl-1-yl) propyl]cyclopentan-2-one, 2-sec-butylcyclohexanone, allyl ionone, α-cetone, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, menthone, methyl-7,3-dihydro-2H-1,5-benzodioxepine-3-one, fenchone, methyl hydroxynaphthyl ketone, and mixtures thereof.

According to the present invention all isomers of a fragrance raw material whether in the form of the pro-accord or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R-(+)-β-citronellol and S-(−)-β-citronellol. Each of these materials separately or as a racemic pair are suitable for use as fragrance raw materials in the present invention. However, those skilled in the art of fragrances, by utilization of the present invention, should not disregard the olfactory differences that individual optical isomers, admixtures of optical isomers or admixtures of positional isomers impart. By way of example, carvone, 2-methyl-5-(1-methylethenyl)-2-cyclohexene-1-one exists as two isomers; d-carvone and l-carvone. d-Carvone is found in oil of caraway and renders a completely different fragrance from l-carvone which is found in spearmint oil. According to the present invention a pro-accord which releases d-carvone will result in a different scent or fragrance than one which releases l-carvone. The same applies to l-carvone. In addition, isomers such as cis/trans isomers, for example, nerol (3,7-dimethyl-cis-2,6-octadien-1-ol) and geraniol (3,7-dimethyl-trans-2,6-octadien-1-ol), are well known to those skilled in the art of perfumery and these two terpene alcohols, which commonly occur as an admixture, have different fragrance characteristics. Therefore, when formulating fragrance raw materials which comprise mixtures of isomers such as nerol/geraniol, the formulator must also take into account whether different sources of raw material have different ratios of isomers.

An example of a preferred pro-accord is 3,7-dimethyl-1,6-octadien-3-yl 3-(β-naphthyl)-3-oxo-propionate having the formula:

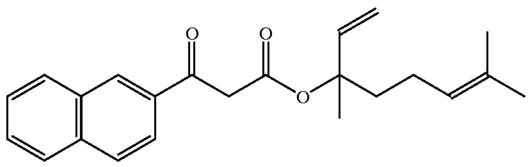

which releases at least the fragrance raw material alcohol, linalool, having the formula:

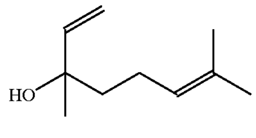

and the fragrance raw material ketone, methyl naphthyl ketone, having the formula:

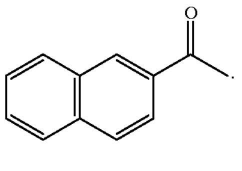

A further example of a preferred pro-accord includes 2,6-dimethyl-7-octen-2-yl 3-(4-methoxyphenyl)-3-oxo-propionate having the formula:

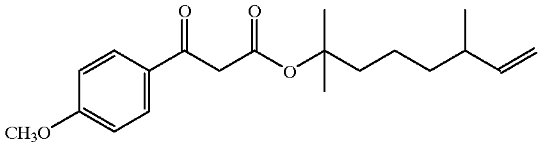

which releases at least the fragrance raw material alcohol, dihydromyrcenol, having the formula:

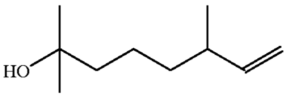

and the fragrance raw material ketone, methyl 4-methoxyphenyl ketone, having the formula:

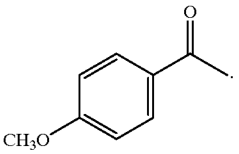

Further non-limiting examples of preferred pro-accords include 3,7-dimethyl-1,6-octadien-3-yl 3-(α-naphthyl)-3-oxo-propionate, [linalyl (1-naphthoyl)acetate], having the formula:

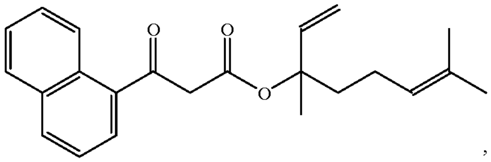

, 2,6-dimethyl-7-octen-2-yl 3-(4-methoxyphenyl)-3-oxo-propionate, [3-(4-methoxyphenyl)-3-oxo-propionic acid dihydromyrcenyl ester], having the formula:

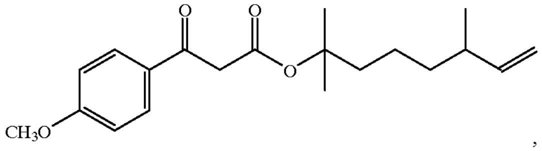

, 2,6-dimethyl-7-octen-2-yl 3-(4-nitrophenyl)-3-oxo-propionate, [3-(4-nitrophenyl)-3-oxo-propionic acid dihydromyrcenyl ester], having the formula:

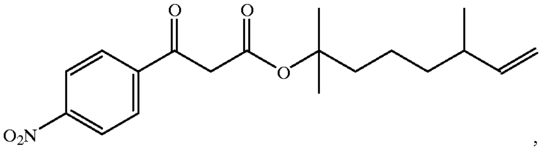

, 2,6-dimethyl-7-octen-2-yl 3-(β-naphthyl)-3-oxo-propionate, [dihydromyrcenyl (2-naphthoyl)acetate], having the formula:

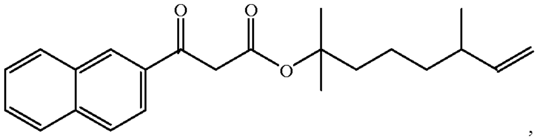

, 3,7-dimethyl-1,6-octadien-3-yl 3-(4-methoxyphenyl)-3-oxo-propionate, [3-(4-methoxyphenyl)-3-oxo-propionic acid linalyl ester], having the formula:

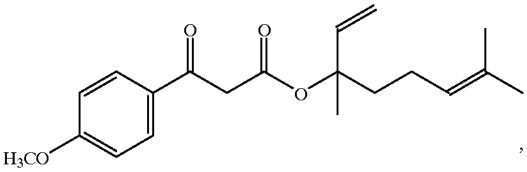

, (α,α-4-trimethyl-3-cyclohexenyl)methyl 3-(β-naphthyl)-3-oxo-propionate, [α-terpinyl (2-naphthoyl)acetate], having the formula:

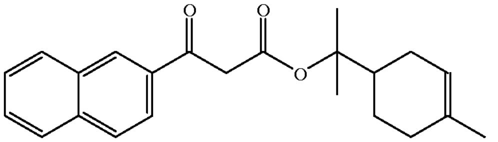

, 9-decen-1-yl 3-(β-naphthyl)-3-oxo-propionate, [9-decen-1-yl (2-naphthoyl)acetate], known alternatively as, rosalva 2'-acetonaphthone, having the formula:

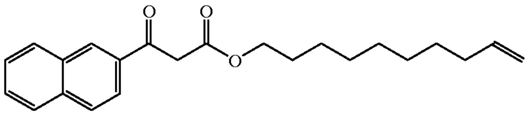

, 3,7-dimethyl-1,6-octadien-3-yl 3-(nonanyl)-3-oxo-propionate, [linalyl (nonanoyl)acetate], known alternatively as, octyl [(linalyl) α-acetyl] ketone, having the formula:

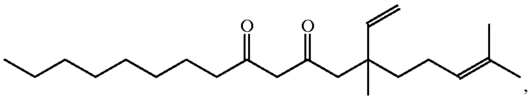

, 3,7-dimethyl-1,6-octadien-3-yl 3-oxo-butyrate, known alternatively as, linalyl acetoacetate, having the formula:

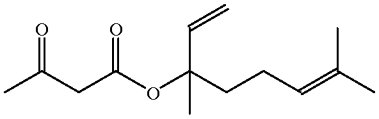

, 2,6-dimethyl-7-octen-2-yl 3-oxo-butyrate, [dihydromyrcenyl acetoacetate], having the formula:

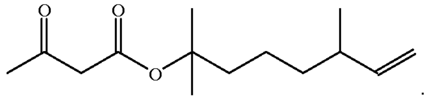

Additional non-limiting examples of preferred pro-fragrances which comprise the fragrance delivery systems of the present invention include cis 3-hexen-1-yl 3-(β-naphthyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof.

Without wishing to be limited by theory, the process by which the pro-accords of the present invention release their fragrance raw materials is not limited to one pathway. In fact, the same molecule under identical conditions may have several equal pathways by which the same or different compounds are released. For example, both nerol and geraniol may be released from an ester which is formed only from geraniol, provided the conditions under which the geraniol to nerol transformation can occur, are present during usage. These conditions can by built into the molecule by the formulator or can be provided by the surrounding environment (i.e. the formulation). In addition, during the process of fragrance raw material release, both the keto-portion and the alcohol-portion of the pro-accords are capable of undergoing chemical transformations which provide a mixture of fragrance notes not subject to inclusion in the original pro-accords. For example, a pro-accord ester which comprises the fragrance raw material alcohol citronellol, can potentially release a mixture of rose oxides by the following scheme:

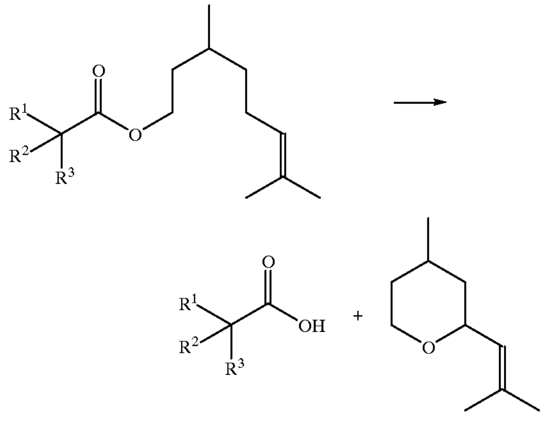

provided that suitable rearrangement conditions are present during usage.

The formulator is not limited to the delivery of one type of fragrance, for example a top, middle, or base fragrance raw material note. Instead a mixture of top notes, a mixture of top and middle notes, or any combination of top, middle and base notes may be delivered in any suitable proportion.

As described herein above, those skilled in the art of preparing fragrance-containing compositions have categorized fragrances into three types based on their relative volatility; top, middle, and base notes. In addition, fragrances are categorized by the odor they produce; some of these descriptors are broad and others are relatively specific. For example, "floral" is a term which connotes odors associated with flowers while the term "lilac" is more specific. Descriptors used by those skilled in the art of perfumes and fragrances are inter alia "rose", "floral", "green", "citrus", "spicy", "honey", and "musk". The sources of these notes are not limited to one chemical class; alcohols can produce "rose", "green", and "musk" scents, while "rose" scents can comprise alcohols, ketones, terpenes, aldehydes, etc.

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. The compositions described herein below, as well as others chosen by the formulator, comprise a fragrance delivery system which utilizes the pro-accords of the present invention to successfully deliver a "balanced fragrance" profile.

It is also recognized by those skilled in the art that descriptors which relate to aesthetic perceptions such as "top", "middle" and "base" notes are relative terms. A fragrance raw material categorized as a top note by one formulator usually has the identical classification among most other Perfumers. The same is true for the middle and base notes, however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Yet apart from this pleasant fragrance, a fragrance delivery system which is used to deliver a scent to a personal care item must meet a number of technical requirements. It must be sufficiently strong, it must be persistent, and it must retain its "essential character" throughout its period of evaporation.

Aside from the changes made to the pro-accord molecules for the purpose of modifying the fragrance profiles which the fragrance delivery systems of the present invention provide, modifications can be made to these pro-accords for the purpose of increasing the formulatability of the materials. The formulator by selecting a suitable $R^1$, $R^2$, or $R^3$ unit, or upon the selection of $R^4$ $R^5$, and $R^6$, can influence the degree and rate at which the pro-accord is deposited upon hair or skin or the manner in which the fragrance delivery system is dispersed within a composition.

The following examples illustrate the β-keto-esters and compositions which comprise the fragrance delivery system of this invention, but are not intended to be limiting thereof.

EXAMPLE 1

Preparation of 3,7-dimethyl-1,6-octadien-3-yl 3-(β-naphthyl)-3-oxo-propionate Lithium diisopropylamide (101.0 mL of a 2.0 M solution, 0.202 mol) is placed into a 500 mL three-necked round-bottomed flask fitted with a magnetic stirrer, internal thermometer, argon inlet, and-addition funnel. The flask is placed in a dry ice-acetone bath. 3,7-Dimethyl-1,6-octadien- 3-yl acetate (linalyl acetate) in the amount of (18.66 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.43 g, 0.090 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and GC analysis and the structure confirmed by mass spectrometry, $^1H$ and $^{13}C$ NMR.

EXAMPLE 2

Preparation of 2,6-dimethyl-7-octen-2-yl 3-(4-methoxyphenyl)-3-oxo-propionate N-Isopropylcyclohexylamine (25.00 g, 0.177 mol) and THF in the amount of 200 mL is placed into a 1000 mL three-necked round-bottomed flask fitted with a magnetic stirrer, internal thermometer, argon inlet, and addition funnel. The flask is placed in a ice-methanol bath cooled to −5° C. and its contents treated with n-butyllithium in the amount of (70.8 mL of a 2.50 M solution, 0.177 mol). The mixture is stirred for 20 min and then cooled to −78° C. 2,6-Dimethyl-7-octen-2-yl acetate (dihydromyrcenyl acetate) in the amount of (17.55 g, 0.089 mol) is dissolved in THF (10 mL) and the resulting solution added to the flask over 45 min. Once addition is complete, the mixture is stirred for an additional 15 min before being treated with a solution p-methoxybenzoyl chloride in the amount of (15.10 g, 0.090 mol) dissolved in THF (25 ml) over 30 min and then stirred for 1 h. The mixture is warmed to 0° C. and then treated with 90 mL of 20% HCl an hour later. The mixture is poured into a separatory funnel containing ether (100 ml) and water (200 ml). The aqueous layer is extracted with ether (100 ml). The combined organic layers are washed with saturated $NaHCO_3$ solution (2×100 ml), water (2×100 ml) and brine (100 ml), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and the structure confirmed by $^1H$ and $^{13}C$ NMR.

EXAMPLE 3

Preparation of 2,6-dimethyl-7-octen-2-yl 3-(4-nitrophenyl)-3-oxo-propionate

Lithium diisopropylamide (121.0 mL of a 2.0 M solution, 0.243 mol) is placed into a 500 mL three-necked round-bottomed flask fitted with a magnetic stirrer, internal thermometer, argon inlet, and addition funnel. The flask is placed in a dry ice-acetone bath. 2,6-Dimethyl-7-octen-2-yl acetate (22.66 g, 0.114 mol) is dissolved in THF (5 mL) and the resulting solution added to the flask over 45 min. Once addition is complete, the mixture is stirred for an additional 15 min. before being treated with a solution of 4-nitrobenzoyl chloride (20.00 g, 0.108 mol) dissolved in THF (25 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 4

Preparation of 2,6-dimethyl-7-octen-2-yl 3-(β-naphthyl)-3-oxo-propionate

Lithium diisopropylamide in the amount of (100.0 mL of a 2.0 M solution, 0.201 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate in the amount of(18.75 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.00 g, 0.089 mol) dissolved in THF (25 mL) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate dissolved in petroleum ether) to give an oil. Purity of the product is determined by thin layer chromatography and the structure confirmed by $^1H$ and $^{13}C$ NMR.

EXAMPLE 5

Preparation of 3,7-dimethyl-1,6-octadien-3-yl 3-(4-methoxyphenyl)-3-oxo-propionate Lithium diisopropylamide (119.0 mL of a 2.0 M solution, 0.238 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (22.04 g, 0.112 mol) is dissolved in THF (5 mL) and the resulting solution added to the flask over 45 min. Once addition is complete, the mixture is stirred for an additional 15 min. before being treated with a solution p-anisoyl chloride (35.00 g, 0.106 mol) dissolved in THF (30 mL) over 30 min. The mixture is warmed to −20° C. and stirred at that temperature for 18 h. After warming to 0° C., the mixture is quenched with 20% HCl (80 mL). The mixture is poured into a separatory funnel containing ether (150 mL) and water (250 mL). The aqueous layer is extracted with ether (50 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a colorless oil having $^1H$ and $^{13}C$ NMR spectra consistent with the desired product.

EXAMPLE 6

Preparation of (α,α-4-trimethyl-3-cyclohexenyl) methyl 3-(β-naphthyl)-3-oxo-propionate Lithium diisopropylamide (171.0 mL of a 2.0 M solution, 0.342 mol) is placed into a 1000 mL three-necked round-bottomed flask fitted with a magnetic stirrer, internal thermometer, argon inlet, and addition funnel. The flask is cooled to −78° C. (α,α-4-Trimethyl-3-cyclohexenyl)methyl acetate (30.00 g, 0.153 mol) is dissolved in THF (10 mL) and the resulting solution added to the flask over 45 min. Once addition is complete, the mixture is stirred for an additional 15 min. before being treated with a solution of 2-naphthoyl chloride (29.00 g, 0.152 mol) dissolved in THF (50 mL) over 30 min. The mixture is warmed to −20° C. and stirred at that temperature for 18 h. After warming to 0° C., the mixture is quenched with 20% HCl (105 mL). The mixture is poured into a separatory funnel containing ether (150 mL) and water (250 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a semi-white solid which is triturated in cold n-pentane to yield a white powder having $^1H$ and $^{13}C$ NMR spectra consistent with the desired product.

EXAMPLE 7

Preparation of 3,7-dimethyl-1,6-octadien-3-yl 3-(α-naphthyl)-3-oxo-propionate

Lithium diisopropylamide (96.3 mL of a 2.0 M solution, 0.193 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (17.81 g, 0.091 mol) is dissolved in THF (5 mL) and the resulting solution added to the flask over 45 min. Once addition is complete, the mixture is stirred for an additional 15 min. before being treated with a solution of 1-naphthoyl chloride (16.82 g, 0.086 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a colorless oil having $^1H$ and $^{13}C$ NMR spectra consistent with the desired product.

EXAMPLE 8

Preparation of cis 3-hexen-1-yl 3-(β-naphthyl)-3-oxo-propionate

Lithium diisopropylamide (133.0 mL of a 2.0 M solution, 0.266 mol) is placed into a 500 mL three-necked round-bottomed flask fitted with a magnetic stirrer, internal thermometer, argon inlet, and addition funnel. The flask is cooled to −78° C. cis 3-Hexenyl acetate (17.80 g, 0.125 mol) is dissolved in THF (10 mL) and the resulting solution added to the flask over 45 min. Once addition is complete, the mixture is stirred for an additional 15 min. before being treated with a solution of 2-naphthoyl chloride (22.51 g, 0.118 mol) dissolved in THF (30 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 9

Preparation of 9-decen-1-yl 3-(β-naphthyl)-3-oxo-propionate

Lithium diisopropylamide (79.8 mL of a 2.0 M solution, 0.160 mol) is placed into a 250 mL three-necked round-bottomed flask fitted with a magnetic stirrer, internal thermometer, argon inlet, and addition funnel. The flask is cooled to −78° C. 9-Decen-1-yl acetate (14.91 g, 0.075 mol) is dissolved in THF (5 mL) and the resulting solution added to the flask over 45 min. Once addition is complete, the mixture is stirred for an additional 15 min. before being treated with a solution of 2-naphthoyl chloride (13.80 g, 0.071 mol) dissolved in THF (25 mL) over 30 min. The mixture is warmed to −20° C. and stirred at that temperature for 18 h. After warming to 0° C., the mixture is quenched with 20% HCl (47 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 10

Preparation of 3,7-dimethyl-1,6-octadien-3-yl 3-(nonanyl)-3-oxo-propionate

Lithium diisopropylamide (133.7 mL of a 2.0 M solution, 0.267 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (24.73 g, 0.126 mol) is dissolved in THF (40 mL) and the resulting solution added to the flask over 45 min. Once addition is complete, the mixture is stirred for an additional 15 min. before being treated with a solution of nonanoyl chloride (21.88 g, 0.119 mol) over 30 min. The mixture is warmed to −20° C. and stirred at that temperature for 18 h. After warming to 0° C., the mixture is quenched with 20% HCl (60 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 11

Preparation of 2,6-dimethyl-7-octen-2-yl 3-(nonanyl)3-oxo-pronionate

Lithium diisopropylamide (75.7 mL of a 2.0 M solution, 0.151 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate (14.14 g, 0.071 mol) is dissolved in THF (20 mL) and the resulting solution added to the flask over 45 min. Once addition is complete, the mixture is stirred for an additional 15 min. before being treated with a solution of nonanoyl chloride (12.38 g, 0.067 mol) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 12

Preparation of 3,7-dimethyl-1,6-octadien-3-yl 3-oxo-butyrate

A mixture of linalool (100 g, 0.648 mol) and 4-dimethylaminopyridine (0.40 g, 3.20 mmol) in a 500 mL three-necked round-bottomed flask fitted with a condenser, argon inlet, addition funnel, magnetic stirrer and internal thermometer is heated to 55° C. Diketene (54.50 g, 0.648 mol) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromatography (elution with dichloromethane) yields the desired product in 92% yield and nearly colorless.

EXAMPLE 13

Preparation of 2,6-dimethyl-7-octen-2-yl 3-oxo-butyrate

A mixture of dihydromyrcenol (37.88 g, 0.240 mol) and 4-dimethylaminopyridine (0.16 g, 1.30 mmol) in a 100 mL three-necked round-bottomed flask fitted with a condenser, argon inlet, addition funnel, magnetic stirrer and internal thermometer is heated to 50–60° C. Diketene (20.16 g, 0.240 mol) is added dropwise in the course of 15 min. The mixture has a slight exotherm and turned from yellow to red during this time. After stirring an additional hour at 50° C., the mixture is cooled to room temperature. At this point, NMR analysis indicates the reaction is complete. Purification of the product mixture by flash chromatography (elution with dichloromethane) yields the desired product in 95% yield as a nearly colorless oil.

EXAMPLE 14

Preparation of 3,7-dimethyl-1,6-octadien-3-yl 3-(β-naphthyl)-3-oxo-propionate Crude 3,7-dimethyl-1,6-octadien-3-yl 3-oxo-butyrate (154.51, 0.648 mol) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to ~1 with 20% HCl. The mixture is transferred to a separatory funnel containing diethyl ether (500 mL) and water (500 mL). The layers are separated and the organic phase is washed with saturated $NaHCO_3$ solution (2×500 mL), dried over $MgSO_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoyl)acetate. A portion of this material is purified by column chromatography (elution with 2.5% ethyl acetate in hexanes) to give the desired product as a light yellow oil.

EXAMPLE 15

Preparation of 3,7-dimethyl-1,6-octadien-3-yl 3-(β-naphthyl-3-oxo-2,2-dimethylpropionate Sodium hydride (2.30 g, 0.057 mol, 60%) and tetrahydrofuran (50 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (8.94 g, 0.025 mol) dissolved in 50 mL of tetrahydrofuran is added dropwise to the flask over 30 min. During addition, the mixture evolves gas. After stirring for 1 h, methyl iodide (7.24 g, 0.051 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 16

Preparation of 3,7-dimethyl-1,6-octadien-3-yl 3-(β-naphthyl)-3-oxo-2-methylpropionate Sodium hydride (3.92 g, 0.098 mol, 60%) and tetrahydrofuran (100 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (15.28 g, 0.044 mol) dissolved in 50 mL of tetrahydrofuran is added dropwise to the flask over 30 min. During addition, the mixture evolves gas. After stirring for 1 h, methyl iodide (10.65 g, 0.075 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 17

Preparation of 3,7-dimethyl-1,6-octadien-3-yl 3-(hexyl)-3-oxo-propionate 3,7-Dimethyl-1,6-octadien-3-yl 3-oxo-butyrate (30.00 g, 0.126 mol), dichloromethane (50 mL) and methyl ethyl ketone (10 mL) are combined in a 500 mL three-necked round-bottomed flask fitted with an internal thermometer, addition funnel, condenser and argon inlet. Calcium hydroxide (9.80 g, 0.132 mol, powdered) is added to the flask and the slurry stirs for 1 h. Heptanoyl chloride (17.84 g, 0.120 mol) in 10 ml of dichloromethane is added over 15 min so as to keep the reaction temperature between 35–40° C. The reaction continues to stir at 35–40° C. for 2 h. Ammonium chloride (7.06 g, 0.132 mol) dissolved in 20 mL of water is added to the flask. After 20 min, concentrated ammonium hydroxide is added to the mixture to adjust the pH to ~9.0. After 1 h, 20% HCl solution is added to drop the pH to ~1.0. After 1 h, the mixture is poured into 300 mL of dichloromethane. The layers are separated and the aqueous phase extracted with 100 mL of dichloromethane. The combine organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 18

Preparation of 3,7-dimethyl-1,6-octadien-3-yl 3-oxo-2-benzylbutyrate

Potassium carbonate (3.92 g, 0.028 mol), 3,7-dimethyl-1,6-octadien-3-yl 3-oxo-butyrate (4.80 g, 0.030 mol), benzyl chloride (4.80 g, 0.038 mol) and acetone (15 mL) are placed in a 50 mL round-bottomed flask fitted with a magnetic stirrer, condenser and argon inlet. The mixture is heated to reflux for 18 h. The cooled mixture is filtered and concentrated by rotary evaporation. The resulting oil is purified on silica gel to yield the desired compound. Structure is confirmed by thin layer chromatography and $^1H$ and $^{13}C$ NMR.

Skin Conditioning Lotions

An example of a skin care composition of the present invention comprises an ester having a total number of carbon atoms in excess of about 28, for example lauryl laurate, lauryl myristate, myristyl myristate, behenyl caprate, cetearyl palmitate, behenyl stearate, more preferably cetearyl palmitate and cetyl stearate.

The present compositions in addition to the esters described herein above, contain an emollient material in an amount such that the amount of ester plus emollient is from about 0.2% to about 25% of the total composition, preferably from about 4% to about 18%. One function of the emollient is to ensure that the ester is plasticized sufficiently to allow it to be in a film-like state on the skin. The emollient in the present compositions is selected from the group consisting of fatty alcohols, esters having fewer than about 24 total carbon atoms (e.g. isopropyl palmitate), branched chain esters having greater than about 24 total carbon atoms (e.g. cetearyl octonate), squalane, liquid or solid paraffins, mixtures of fatty acids and squalane, mixtures of fatty acids and liquid or solid paraffins and mixtures thereof. The aforementioned esters, those having fewer than 24 carbon atoms or branched and having more than 24 carbon atoms, if used as an emollient should preferably be used in an mount equal to about a third of the long chain ester. The particular emollient selected depends in part on the particular ester selected since proper plasticization, as indicated above, is desired. The emollient for the esters having more than 28 carbon atoms is preferably selected from the group consisting of squalane, liquid or solid paraffins and mixtures of fatty alcohols with squalane or paraffins. Typical fatty alcohols and fatty acids useful in the present compositions include those having from 12–22 carbon atoms such as cetyl alcohol, myristyl alcohol, stearyl alcohol, stearic acid and palmitic acid. Paraffins include, for example, mineral oil, petrolatum and paraffin wax. It is preferred that distilled water be used in the present compositions.

Optional Components

Oil Phase Components

In addition to the long chain esters, emollients and emulsifiers described previously, the oil phase of the present compositions may contain a variety of materials including:

(a) Esters not meeting the requirements for the long chain ester and not present as an emollient, supra, such as oleyl oleate, isostearyl isostearate, isopropyl lanolate, isopropyl myristate, butyl stearate, myristyl lactate and 2-ethyl hexyl palmitate;

(b) Oils such as castor oil, jojoba oil, cottonseed oil, peanut oil and sesame oil;

(c) Waxes such as ceresin wax, carnuba wax, beeswax and castor wax;

(d) Lanolin, its derivatives and components such as acetylated lanolin, lanolin alcohols and lanolin fatty acids. Lanolin fatty acids are described in U.S. Pat. No. Re. 29,814, Oct. 24, 1978 to W. E. Snyder incorporated herein by reference.

(e) Polyalkylenes such as hydrogenated polyisobutene and polyethylene; and (f) Sterols such as cholesterol and phytosterol.

These optional oil phase materials may comprise up to about 80% of the oil phase, preferably up to about 35%. When used at these levels, the optional components do not impair the occlusive nature of the compositions and add to the composition's total cosmetic performance.

Water Phase Components

The water phase of the compositions may contain many different materials including:

(a) Humectants, such as sorbitol, glycerine, propylene glycol, alkoxylated glucose and hexanetriol at a level of from about 1% to about 20%.

(b) Thickening agents such as carboxyvinyl polymers, ethyl cellulose, polyvinyl alcohol, carboxymethyl cellulose, vegetable gums and clays such as Veegum.RTM. (magnesium aluminum silicate, R. T. Vanderbilt, Inc.) at a level of from about 0.01% to about 6%;

(c) Proteins and polypeptides at a level of from about 0.1% to about 3%;

(d) Preservatives such as the methyl, ethyl, propyl and butyl esters of hydroxybenzoic acid (Parabens-Mallinckrodt Chemical Corporation) EDTA and imidazolidinyl urea (Germall 115-Sutton Laboratories) at a level of from about 0.2% to about 2.5%; and (e) An alkaline agent such as sodium hydroxide to neutralize, if desired, part of the fatty acids or thickener which may be present.

All of the percentages of these additional water phase components are of the total composition.

The present compositions may also contain agents suitable for aesthetic purposes such as dyes. The compositions of the present invention are preferably substantially free of materials which adversely affect their performance. Therefore, such things as polyethylene glycols are preferably present only at levels below about 1% of the total composition. The pH of the present compositions is preferably in the range of about 7.5–10.

METHOD OF MANUFACTURE

The compositions of the present invention generally have a lotion consistency and may be in the form of oil-in-water or water-in-oil emulsions with the former being preferred because of their more pleasing cosmetic properties. The compositions of the present invention are preferably made by the method comprising the steps of;

a) preparing the oil phase;

b) preparing the water phase; and c) adding the oil phase to the water phase.

Step (a) is carried out by heating the oil phase materials to a temperature of about 75° C. to about 100° C. Step (b) is carried out by heating the water phase materials to a temperature about the same as that of the oil phase. The emulsion is formed by slowly adding the oil phase prepared in step (a) to the water phase prepared in step (b) with stirring. The pro-accords which comprise the fragrance delivery system or other ingredients may be added to the phase in which they are soluble prior to the mixing of the two phases or added directly to the mixed water and oil phases.

In addition to the fragrance-containing compositions for use on human skin, the pro-accords of the present invention are also suitable for use in any odor controlling or fragrance mediating application. A example of this odor control capacity is animal litter and odor control articles useful in lining the cages, stalls, and other living areas of domesticated animals. For example, U.S. Pat. No. 5,339,769 Toth et al., issued Aug. 23, 1994 describes a process for making an absorbent composition which can well accommodate the pro-accord materials of the present invention.

An example of a suitable litter material which comprises the pro-accords of the present invention can be formed by the following process.

A Glatt fluid bed granulator is charged with 1,0000 g of bentonite clay (90% of the particles being greater than 420 microns) and 10 g of a cellulose ether (Methocel™ K15M Premium, a cellulose ether having a viscosity of 15,000 centipoise (cps) as a 2% aqueous solution). The granulator is started an the product temperature is brought up to about 40° C. (outlet temperature). When the outlet temperature reaches about 40° C., atomized water is sprayed onto the moving powders within the granulator, During the granulation process, inlet air temperature is maintained at 70° C. to 80° C.; air atomization pressure is 28–35 psi; and the spraying cycle is for 45 seconds with a 15 second shaking time.

The clay/cellulose ether agglomerates swell over time. The water hydrates the cellulose ether polymer which produces adhesion to form the granule. At this time it is more advantageous to introduce the pro-accord materials and other aesthetic fragrances. The formation of the granule promotes aggregation of the small sized particles of the inert substrate, e.g. clay particles of about 50 to 600 microns. The formation of a granule significantly reduces the quality of dust in the final product while the litter forms an agglomerate when wetted.

In an alternative embodiment of the clay-based litter box articles/pro-accord admixture, once the clay particles have been formed, a concentrated solution, or an carrier alcohol-based admixture of the pro-accords may be delivered to the surface of the granule by a suitable means.

A deodorant gel stick of the present invention having the composition given below, and being essentially free of water, is prepared as follows.

TABLE V

| | Weight % | | |
|---|---|---|---|
| Ingredients | 19 | 20 | 21 |
| Dipropylene glycol | 39.85 | 51.95 | 75.10 |
| Sodium Stearate | 5.50 | 5.50 | 5.50 |
| PPG-3 myristyl ether | 29.40 | 25.33 | 15.00 |
| Cyclomethicone-D5 | 21.00 | 13.33 | — |
| Ethanol (absolute; 200 proof) | 1.80 | 1.44 | 1.95 |
| Zinc pyrithione[1] | 0.05 | 0.05 | 0.05 |
| Pro-accord[2] | 2.40 | 2.40 | 2.40 |

[1]Powder form commercially available from Olin.
[2]Pro-accord admixture comprising 75% of the pro-accord from Example 1 and 25% of the pro-accord from Example 4.

All of the above materials, except the fragrance pro-accord, are vigorously mixed and heated to about 121° C. until the mixture is clear. The mixture is them cooled to about 80° C. and the pro-accord is added with stirring. The mixture is poured into stick molds and cooled to room temperature forming the deodorant gel stick compositions of the present invention.

A personnel cleanser composition is prepared by combining the following ingredients using conventional mixing techniques.

TABLE VI

| | Weight % | | | |
|---|---|---|---|---|
| Ingredients | 22 | 23 | 24 | 25 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |
| Methylparaben | 0.200 | 0.200 | 0.200 | 0.200 |
| $C_{10}$–$C_{30}$ alkyl acrylate crosspolymer[1] | 0.150 | 0.150 | 0.150 | 0.150 |
| Carbomer 954[2] | 0.250 | 0.250 | 0.250 | 0.250 |

TABLE VI-continued

| | Weight % | | | |
|---|---|---|---|---|
| Ingredients | 22 | 23 | 24 | 25 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide[3] | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil[4] | — | 5.00 | — | — |
| Phase E | | | | |
| Phenoxyethanol | 0.5 | 0.5 | — | 0.5 |
| Pro-accord[5] | 1.5 | 1.5 | — | — |
| Pro-accord[6] | — | — | 2.20 | 1.5 |
| Phase F | | | | |
| Glucose amide | 0.96 | 0.96 | 0.96 | 0.96 |

[1]Available as Pemulen ® from B. F. Goodrich Corporation.
[2]Available as Carbomer ® 954 from B. F. Goodrich Corporation.
[3]As a 50% aqueous solution.
[4]Light mineral oil available as Drakeol 5 from Penreco, Dickenson, TX.
[5]Pro-accord according to Example 1.
[6]Pro-accord according to Example 9.

The above Examples 22–25 can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C. and added to the emulsion, which is cooled to room temperature. The resulting cleansing composition is useful for cleansing the skin. The emulsion de-emulsifies upon contact with the skin.

What is claimed is:

1. A composition applied to skin having increased fragrance retention and fragrance longevity, comprising:

a) from about 0.01% by weight, of a β-ketoester having the formula:

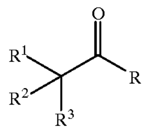

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

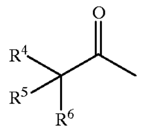

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^4$, $R^5$, and $R^6$ can be taken together to form $C_6$–$C_{30}$ substituted or unsubstituted aryl; and mixtures thereof;

b) from about 0.01% by weight, of one or more adjunct ingredients selected from the group consisting of surfactants, emollients, bactericides, gelling agents, desiccants, propellants, dyes, colorants, ointment bases, lanolin, antiperspirants, mineral oil, talc, abrasives, optical brighteners, phase stabilizing agents, absorbents, and mixtures thereof; and c) the balance carriers.

2. A composition according to claim 1 comprising from about 0.01% to about 15% by weight of a β-ketoester.

3. A composition according to claim 2 comprising from about 1% to about 5% by weight of a β-ketoester.

4. A composition according to claim 3 comprising from about 0.1% to about 1% by weight of a β-ketoester.

5. A composition according to claim 1 wherein $R^1$ has the formula:

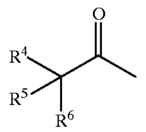

$R^2$, $R^3$, $R^4$ and $R^5$ are each hydrogen; and $R^6$ is hydrogen, $C_1$–$C_{16}$ substituted or unsubstituted linear alkyl, $C_3$–$C_{16}$ substituted or unsubstituted branched alkyl, and mixtures thereof.

6. A composition according to claim 1 wherein $R^1$ has the formula:

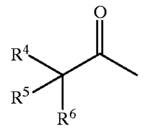

$R^2$ and $R^3$ are each hydrogen, $R^4$, $R^5$ and $R^6$ are taken together to form $C_6$–$C_{30}$ substituted or unsubstituted phenyl, naphthyl, and mixtures thereof.

7. A composition according to claim 1 wherein said β-ketoester is 3,7-dimethyl-1,6-octadien-3-yl 3-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof.

8. A composition according to claim 7 wherein said β-ketoester is 3,7-dimethyl-1,6-octadien-3-yl 3-(β-naphthyl)-3-oxo-propionate.

9. A composition according to claim 1 wherein the adjunct ingredients are selected from the group consisting of dispersents, enzymes, dyes, perfumes, colorants, filler salts, hydrotropes, fluorescers, fabric conditioners, lanolin, hydrolyzable surfactants, preservatives, anti-oxidants, chelants, stabilizers, anti-shrinkage agents, germicides, fungicides, anti corrosion agents, pharmaceutical actives, and mixtures thereof.

10. An antiperspirant composition comprising:

a) from about 0.01% by weight, of a β-ketoester having the formula:

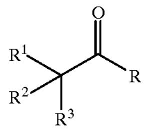

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

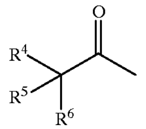

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^4$, $R^5$, and $R^6$ can be taken together to form $C_6$–$C_{30}$ substituted or unsubstituted aryl; and mixtures thereof;

b) from about 0.5% to about 35% by weight, of an antiperspirant active;

c) from about 0.5% to about 25% by weight, of a structuring agent;

d) from about 10% to about 95% by weight, of a carrier; and e) the balance adjunct ingredients.

11. A composition according to claim 10 wherein said β-ketoester is 3,7-dimethyl-1,6-octadien-3-yl 3-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof.

12. A method for providing human skin or hair with extended fragrance benefits comprising the step of contacting human skin or hair with a composition comprising:

a) from about 0.01% by weight, of a β-ketoester having the formula:

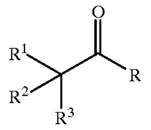

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

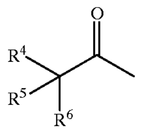

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^4$, $R^5$, and $R^6$ can be taken together to form $C_6$–$C_{30}$ substituted or unsubstituted aryl; and mixtures thereof;

b) from about 0.01% by weight, of one or more adjunct ingredients selected from the group consisting of surfactants, emollients, bactericides, gelling agents, desiccants, propellants, dyes, colorants, ointment bases, lanolin, antiperspirants, mineral oil, talc, abrasives, optical brighteners, phase stabilizing agents, absorbents, and mixtures thereof; and c) the balance carriers.

13. A method according to claim 12 comprising from about 0.01% to about 15% by weight of a β-ketoester.

14. A method according to claim 13 comprising from about 1% to about 5% by weight of a β-ketoester.

15. A method according to claim 14 comprising from about 0.1% to about 1% by weight of a β-ketoester.

16. A method according to claim 12 wherein $R^1$ has the formula:

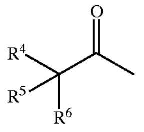

$R^2$, $R^3$, $R^4$ and $R^5$ are each hydrogen; and $R^6$ is hydrogen, $C_1$–$C_{16}$ substituted or unsubstituted linear alkyl, $C_3$–$C_{16}$ substituted or unsubstituted branched alkyl, and mixtures thereof.

17. A method according to claim 12 wherein $R^1$ has the formula:

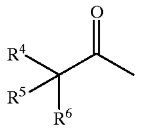

$R^2$ and $R^3$ are each hydrogen, $R^4$, $R^5$ and $R^6$ are taken together to form $C_6$–$C_{30}$ substituted or unsubstituted phenyl, naphthyl, and mixtures thereof.

18. A method according to claim 12 wherein said β-ketoester is 3,7-dimethyl-1,6-octadien-3-yl 3-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate,3,7-dimethyl-2,6-octadienyl 3-heptyl-3-oxo-propionate, and mixtures thereof.

19. A method according to claim 18 wherein said β-ketoester is 3,7-dimethyl-1,6-octadien-3-yl 3-(β-naphthyl)-3-oxo-propionate.

20. A method according to claim 12 wherein the adjunct ingredients are selected from the group consisting of dispersents, enzymes, dyes, perfumes, colorants, filler salts, hydrotropes, fluorescers, fabric conditioners, lanolin, hydrolyzable surfactants, preservatives, anti-oxidants, chelants, stabilizers, anti-shrinkage agents, germicides, fungicides, anti corrosion agents, pharmaceutical actives, and mixtures thereof.

* * * * *